(12) United States Patent
Castillo et al.

(10) Patent No.: US 7,458,949 B2
(45) Date of Patent: Dec. 2, 2008

(54) FLEXIBLE TETHER MEMBER CONNECTING A KNEE BRACE TO A BOOT

(76) Inventors: David Castillo, 26446 Bautista, Mission Viejo, CA (US) 92692; James Castillo, 8300 Bat Canyon, Los Almos, CA (US) 93440

( * ) Notice: Subject to any disclaimer, the term of this patent is extended or adjusted under 35 U.S.C. 154(b) by 208 days.

(21) Appl. No.: 11/396,886

(22) Filed: Apr. 3, 2006

(65) Prior Publication Data
US 2007/0232977 A1 Oct. 4, 2007

(51) Int. Cl.
A61F 5/00 (2006.01)
A61F 13/00 (2006.01)
A61F 5/37 (2006.01)

(52) U.S. Cl. .............................. 602/23; 602/26; 602/62; 128/882

(58) Field of Classification Search .................... 602/23, 602/16, 26, 27, 63, 24, 28, 6, 62; 482/91, 482/124; 36/89, 140; 182/120; 128/882; 2/22, 23, 24
See application file for complete search history.

(56) References Cited

U.S. PATENT DOCUMENTS

| | | | |
|---|---|---|---|
| 2,883,982 A | 4/1959 | Rainey | |
| 3,900,898 A | 8/1975 | Ackerman | |
| 3,902,482 A | 9/1975 | Taylor | |
| 3,928,872 A | 12/1975 | Johnson | |
| 4,136,404 A | 1/1979 | Lange | |
| 4,450,832 A * | 5/1984 | Waddell | 602/16 |
| 4,800,629 A * | 1/1989 | Ikeda | 24/170 |
| 5,222,279 A * | 6/1993 | Frano et al. | 24/625 |
| 6,461,318 B2 | 10/2002 | Freeman | |
| 6,464,657 B1 | 10/2002 | Castillo | |
| 6,689,080 B2 | 2/2004 | Castillo | |
| 6,746,248 B2 * | 6/2004 | Eastwood | 434/253 |
| 6,793,641 B2 | 9/2004 | Freeman | |
| 6,796,951 B2 | 9/2004 | Freeman | |
| 6,962,571 B2 | 11/2005 | Castillo | |
| 7,117,569 B2 * | 10/2006 | Bledsoe | 24/593.11 |
| 2007/0126211 A1 * | 6/2007 | Moerke et al. | 280/728.2 |

* cited by examiner

Primary Examiner—Patricia Bianco
Assistant Examiner—Ophelia Hawthorne
(74) Attorney, Agent, or Firm—Stetina Brunda Garred & Brucker

(57) ABSTRACT

The invention provides a device for protecting ligaments in a knee joint of a user. The device includes a knee brace positionable about a knee joint of a user and a boot wearable on a foot of a user. Additionally, the device includes a flexible tether member including a first coupling element coupled to the knee brace and a second coupling element coupled to the boot. The boot and knee brace are attachable and detachable via the first and second coupling elements. The flexible tether member is adjustable in length to dispose the flexible tether member in tension at least in a portion of a maximum foot range of rotation, where the maximum foot range of rotation of the user's foot relative to the knee joint causes hyperextension of a knee ligament.

2 Claims, 2 Drawing Sheets

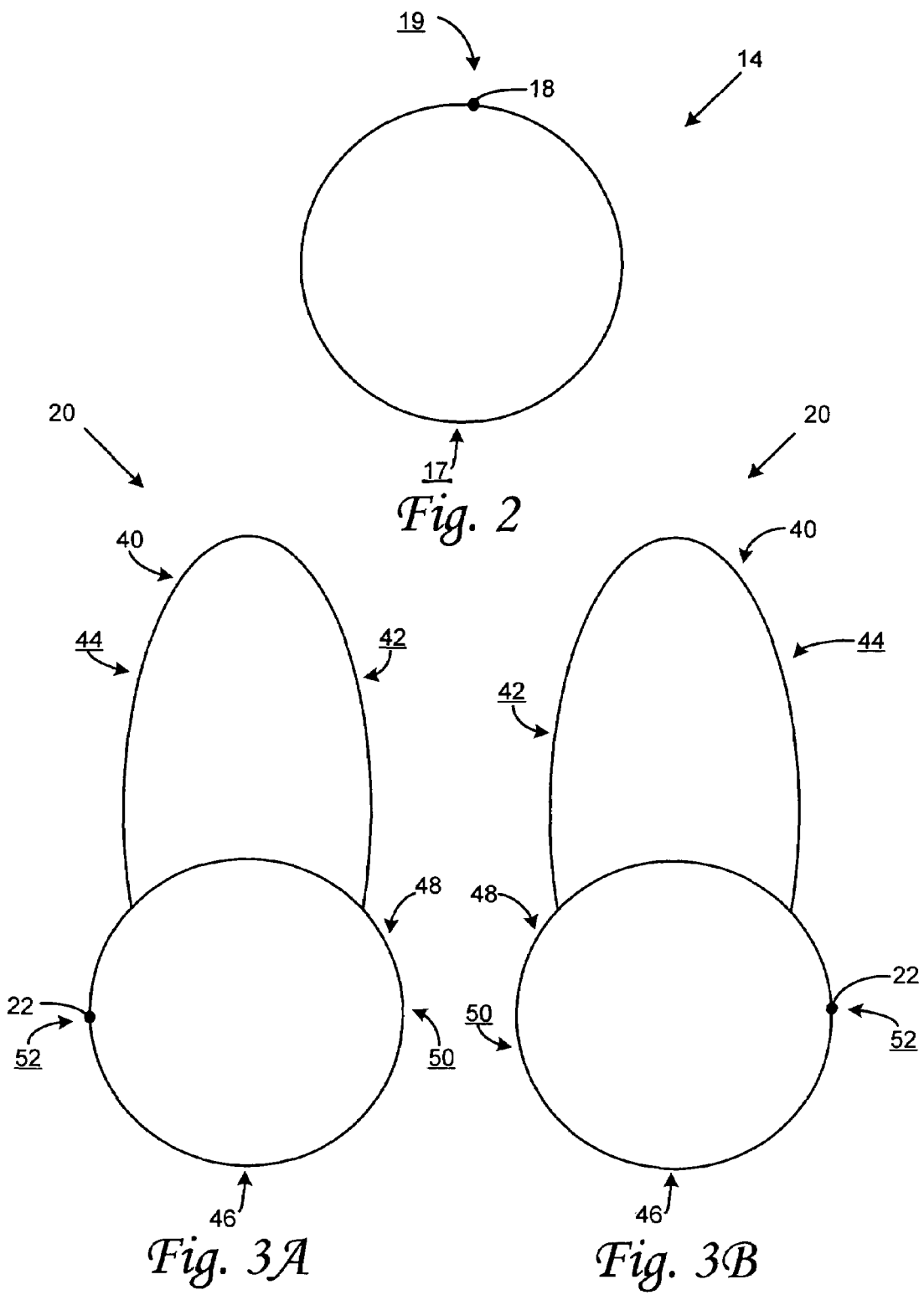

FLEXIBLE TETHER MEMBER CONNECTING A KNEE BRACE TO A BOOT

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Field of Invention

This invention relates in general to a device for protecting the ligaments in a knee joint. Specifically, a knee brace and boot are attachable and detachable via a flexible tether member having a first coupling element coupled to a knee brace and a second coupling element coupled to a boot. The flexible tether member is adjustable in length to dispose the flexible tether member in tension at least within a portion of the range of rotation of a user's foot relative to the user's knee joint causing hyperextension of a knee ligament.

2. Description

The knee joint is one of the body's most delicate joints making it prone to injury. The femur, tibia, and fibula are the bones within the leg that comprise the knee joint. The bones are stabilized by four ligaments. Two collateral ligaments are located on the outside of the knee and control the lateral motion of the knee. The anterior cruciate ligament (ACL) and posterior cruciate ligament (PCL) control rotation of the knee as well as the forwards and backwards motion of the knee.

Injury to the knee joint can occur when at least one of the above-mentioned ligaments tears, either partially or completely. Such an injury may occur during contact or pivoting activities. For that reason, sports related activities are one of the leading causes of injury to the knee. In order to reduce one's risk of sustaining such an injury, athletes wear knee braces. Knee braces provide support to the knee joint and mitigate the stress applied to the ligaments resulting from direct contact.

One group of athletes most susceptible to knee injuries is motocross riders. Motocross is a very physically demanding sport. Motocross riders ride their bikes at high speeds over and around obstacles through winding courses. During a race, the rider is subjected to bumps from the other riders as well as hard landings, which may toss the rider off his bike. Rough landings and accidents may place a lot of stress on a motocross rider's knee ligaments. Therefore, most riders wear knee braces to protect their knees from injury.

Although motocross riders are likely to injure their ligaments due to forces directly applied to the knee joint, the riders are also prone to ligament tears due to pivoting activity, which a knee brace alone may not prevent. For instance, when a rider's foot rotates or pivots independently from the rider's knee joint, a strain is applied to the knee ligaments. If the rotation of the foot is severe, the knee ligaments will hyperextend or tear. Such activity is likely to occur in motocross when a rider makes a turn. As the rider maneuvers his bike through a turn, the rider leans into the turn. Consequently, the rider's inside foot is lowered toward the dirt. On some occasions, the rider's toe catches the dirt causing the rider's foot to rotate independently from the knee joint, imparting a strain on the rider's knee ligaments, specifically the ACL.

A knee brace will not prevent a strain from being applied to the ligaments when the foot rotates independently from the knee joint. A knee brace can prevent lateral motion, as well as forward and backward motion of the knee joint, however, it is not designed to protect the ligaments from rotation. In view of these drawbacks, it is apparent that there is a need in the art for a device for protecting the ligaments in a knee joint from rotation-type injuries.

BRIEF SUMMARY

According to an aspect of the present invention, there is provided a device for protecting ligaments in a knee joint of a user. The device includes a knee brace positionable about a user's knee joint. The knee brace comprises an upper frame member, a lower frame member having a brace connection point, and a joint member pivotally connected to the upper and lower frame members. The device further includes a boot wearable on the user's foot, the boot having a boot connection point. Additionally, the device also includes a flexible tether member. The flexible tether member includes a first coupling element coupled to the knee brace at the brace connection point. The flexible tether member also includes a second coupling element coupled to the boot at the boot connection point. The boot and knee brace are attachable and detachable via the first and second coupling elements. The flexible tether member is adjustable in length to dispose the flexible tether member in tension at least in a portion of a maximum foot range of rotation, where the maximum foot range of rotation of the user's foot relative to the knee joint causes hyperextension of a knee ligament.

According to various embodiments of the present invention, the first coupling element may include a first fastening portion and a first linking portion. The first fastening portion couples the first coupling element with the knee brace at the brace connection point. In addition, the second coupling element may include a second fastening portion and a second linking portion. The second fastening portion couples the second coupling element with the boot at the boot connection point. The first and second linking portions may be cooperatively engageable. In the preferred embodiment of the present invention the first and second linking portions are male and female linking structures, where the first linking portion is a male linking structure and the second linking portion is a female linking structure.

In another embodiment of the present invention the first coupling element may be further comprised of a flexible body portion connected to the first fastening portion and the first linking portion. The flexible body portion may be comprised of a plastic material. Preferably, the flexible body portion is comprised of a woven plastic material.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 2 is a top view of a lower frame member of the knee brace, illustrating the brace connection point located on a front surface of the lower frame member.

FIG. 3A is a top view of a left boot, the boot having a boot toe portion and a boot leg portion and a boot connection point located on a lateral side of the boot leg portion.

FIG. 3B is a top view of a right boot, the boot having a boot toe portion and a boot leg portion and a boot connection point located on a lateral side of the boot leg portion.

DETAILED DESCRIPTION

Figure 1:
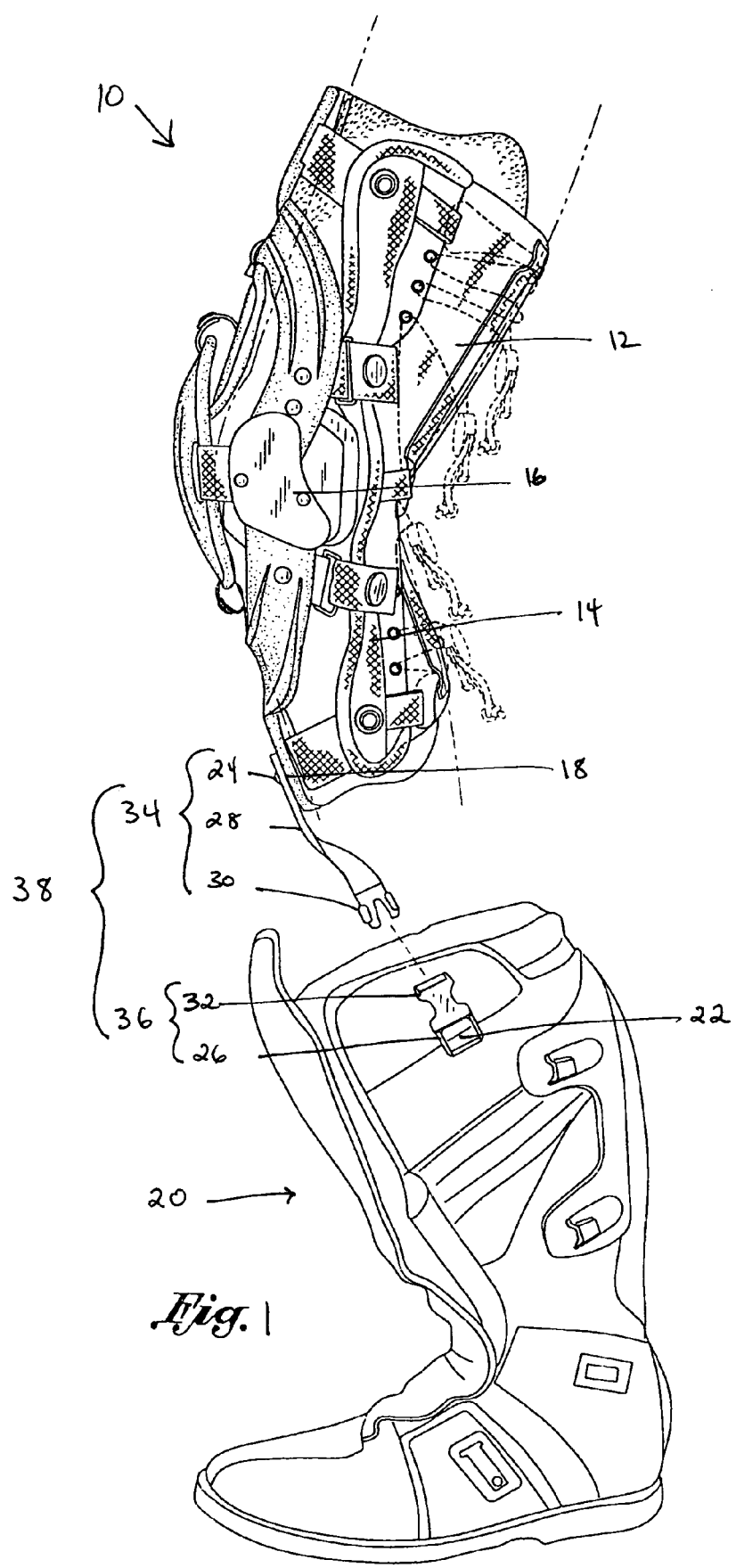
FIG. 1 is a side view of a knee brace, a boot, and a flexible tether member, the boot and knee brace being attachable and detachable via the flexible tether member, the flexible tether member being adjustable in length to dispose the flexible tether member in tension at least in a portion of the maximum foot range of rotation.

The ligaments holding a knee joint together are capable of withstanding a minimal level of tension. The ligaments may be placed in tension when a person's foot rotates independently from the corresponding knee joint. If the foot rotates independently from the knee joint to a point where the knee ligaments begin to hyperextend, the rotation of the foot has exceeded a maximum foot range of rotation. The present invention is a device which limits independent rotation of the foot relative to the knee joint to prevent rotation beyond the maximum foot range of rotation.

Referring to FIG. 1, there is provided a device for protecting ligaments in a knee joint of a user. The device includes a knee brace 10 positionable about a user's knee joint. The knee brace 10 comprises an upper frame member 12, a lower frame member 14 having a brace connection point 18, and a joint member 16 pivotally connected to the upper and lower frame members 12, 14. The device further includes a boot 20 wearable on the user's foot, the boot 20 having a boot connection point 22. Additionally, the device also includes a flexible tether member 38. The flexible tether member 38 includes a first coupling element 34 and a second coupling element 36. The first coupling element 34 is coupled to the knee brace 10 at the brace connection point 18 and the second coupling element 36 is coupled to the boot 20 at the boot connection point 22. The boot 20 and knee brace 10 are attachable and detachable via the first and second coupling elements 34, 36. The flexible tether member 38 is adjustable in length to dispose the flexible tether member 38 in tension at least in a portion of a maximum foot range of rotation, wherein the maximum foot range of rotation of the user's foot relative to the knee joint causes hyperextension of a knee ligament.

The first coupling element 34 of the flexible tether member 38 further includes a first fastening portion 24 and a first linking portion 30. The first fastening portion 24 couples the first coupling element 34 to the knee brace 10 at the brace connection point 18. Correspondingly, the second coupling element 36 of the flexible tether member 38 includes a second fastening portion 26 and a second linking portion 32. The second fastening portion 26 couples the second coupling element 36 to the boot 20 at the boot connection point 22. In the preferred embodiment of the present invention, the first and second coupling elements 34, 36 are fixedly coupled to the knee brace 10 and boot 20 via the first and second fastening portions 24 26, respectively. In such an embodiment, the first and second fastening portions 24, 26 may be a rivet, nail, or bonding agent capable of fixedly coupling the first and second coupling elements 34, 36 to the knee brace 10 and boot 20. However, there may be alternative embodiments of the invention where the first and/or second coupling elements 34, 36 are detachably coupled to the knee brace 10 or boot through the first and second fastening portions 24, 26. For example, the first and/or second fastening portions 24, 26 may be represented by a pin having a spring-loaded locking mechanism which may be placed through a hole in the knee brace 10 or boot 20, the hole being located at the brace or boot connection point 18, 22, thereby allowing the flexible tether member 38 to be detachably coupled to the knee brace 10 and/or boot 20.

The location of the brace 18 and boot connection points 18, 22 are located relative to one another such that the flexible tether member 38 is disposed in tension at least in a portion of the maximum foot range of rotation. FIG. 2 shows a top view of the lower frame member 14 having a front side 19 and a rear side 17. As is shown in FIG. 2, the brace connection point 18 is preferably located on the front side 19 of the lower frame member 14. FIGS. 3A and 3B show a top view of a left and right boot 20, respectively. Each boot 20 has a boot toe portion 40 with a medial side of the boot toe portion 42 and a lateral side of the boot toe portion 44. The boot also includes a leg portion 48 with a medial side of the boot leg portion 50 and a lateral side of the boot leg portion 52. As is shown in FIGS. 3A and 3B, the boot connection point 22 is preferably located on the lateral side of the boot leg portion 52. By having the boot connection point 22 located on the lateral side of the boot leg portion 52 and the brace connection point 18 located on the front side 19 of the lower frame member 14, the flexible tether member 38 may be adjusted to dispose the flexible tether member 38 in tension within a portion of the maximum foot range of rotation. Preferably, the flexible tether member 38 extends across the user's leg from the front side 19 of the lower frame member 14 to the lateral side of the boot leg portion 52 to integrate the knee brace 10 with the boot 20. The knee brace 10 will then rotate with the boot 20, thereby safely transmitting the rotational force to the user's thigh. Other embodiments of the invention may include different locations for the brace and boot connection points 18, 22. However, the location of the brace connection point 18 must be located relative to the boot connection point 22 such that the flexible tether member 38 may be disposed in tension at least in a portion of the maximum foot range of rotation.

The knee brace 10 and boot 20 are attachable and detachable via the first and second coupling elements 34, 36. The first and second coupling elements 34, 36 are attachable and detachable via cooperatively engageable first and second linking portions 30, 32. In the preferred embodiment, the first and second linking portions 30, 32 are cooperatively engageable male and female linking structures, where the male linking structure is included on the first coupling element 34, and the female linking structure is included on the second coupling element 36. However, alternative embodiments may include the female linking structure on the first coupling element 34 and the male linking structure on the second coupling element 36. There may also be alternative embodiments of the first and second linking portions 34, 36, which may include hook and loop fasteners, and buckle and strap fasteners to name a few. In addition, there may be other embodiments of the invention in which one of the first or second linking portions 30, 32 is a slot and the other linking portion may pass through the slot and engages with itself. For example, the second linking portion 32 may be a slot, and the first linking portion 30 may have both hook and loop fasteners located on it. In such an embodiment the hook fasteners of the first linking portion 30 pass through the slot of the second linking portion 32, and engage with loop fasteners located on the first linking portion 30.

The flexible tether member 38 may also include a flexible body portion 28. Preferably, the flexible body portion is included on the first coupling element 34. The flexible body portion 28 connects to the first fastening portion 24 and the first linking portion 30. The length of the flexible body portion 28 may be adjustable, thereby providing for an adjustable length of the flexible tether member 38. The flexible body portion 28 may be comprised of a plastic material. Preferably, the flexible body portion 28 is comprised of a woven plastic material such as woven nylon. Alternative embodiments of the invention may include a flexible body portion 28 on the second coupling element 36, where the flexible body portion 28 is connected to the second fastening portion 26 and the second linking portion 32. Additional embodiments may include a flexible body portion 28 solely on the second coupling element 36, or on both the first and second coupling elements 34, 36.

The flexible tether member 38 integrates the knee brace 10 to the boot 20. Most boots 20 extend vertically around a rider's calf to a point just below the rider's knee, especially motocross boots. In these cases, the flexible tether member 38 would be relatively short, as there would not be much distance between the boot 20 and the knee brace 10. However, not all boots 20 extend to a point just below the knee. In short boot or shoe applications, the flexible tether member 38 may be extended by spiraling around the rider's calf down to the shoe. The shoe would be connected to the knee brace 10 via the flexible tether member 38, thereby protecting the rider from injury as discussed above.

It is understood that athletes, motocross riders in particular, have been wearing knee braces 10 and boots 20 for some time. Therefore, the present invention is capable of being retrofitted onto a user's existing knee brace 10 and boot 20 at the brace and boot connection points 18, 22, respectively. The knee brace 10 and boot 20 may be retrofitted by drilling a hole at the brace and boot connection points 18, 22 to provide for an attachment point for the first and second fastening portions 24, 26. Where the first and second fastening portions 24, 26 are bonding agents capable of being applied directly to an outer surface of the knee brace 10 or boot 20, a hole is not required.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A device for protecting ligaments in a knee joint of a user, wherein a maximum foot range of rotation of a foot of the user relative to the knee joint causes hyperextension of a ligament within the knee joint, the device comprising:
   a knee brace positionable about a knee joint of a user, the knee brace including:
      an upper frame member;
      a lower frame member having a brace connection point; and
      a joint member pivotally connected to the upper and lower frame members;
   a boot wearable on the foot of the user, the boot having a boot connection point, the boot being rotatable relative to the knee brace to rotate the boot connection point relative to the brace connection point; and
   a flexible tether member having:
      a first coupling element coupled to the knee brace at the brace connection point, the first coupling element including a first fastening portion and a first linking portion defining a male linking structure, the first fastening portion coupling the first coupling element with the knee brace at the brace connection point; and
      a second coupling element coupled to the boot at the boot connection point, the second coupling element including a second fastening portion and a second linking portion defining a female linking structure, the second fastening portion coupling the second coupling element with the boot at the boot connection point, the first and second linking portions being cooperatively engageable, the boot and knee brace being attachable and detachable via the first and second coupling elements, the flexible tether member being disposable in tension to mitigate rotation of the boot connection point relative to the brace connection point beyond the maximum foot range of rotation.

2. A device for protecting ligaments in a knee joint of a user, wherein a maximum foot range of rotation of a foot of the user relative to the knee joint causes hyperextension of a ligament within the knee joint, the device comprising:
   a knee brace positionable about a knee joint of a user to provide lateral support to the knee joint, the knee brace including:
      an upper frame member;
      a lower frame member having a brace connection point; and
      a joint member pivotally connected to the upper and lower frame members;
   a boot wearable on the foot of the user, the boot having a boot connection point, the boot being rotatable relative to the boot to rotate the boot connection point relative to the brace connection point; and
   a flexible tether member having:
      a first coupling element coupled to the knee brace at the brace connection point, the first coupling element including a first fastening portion and a first linking portion defining a male linking structure, the first fastening portion coupling the first coupling element with the knee brace at the brace connection point; and
      a second coupling element coupled to the boot at the boot connection point, the second coupling element including a second fastening portion and a second linking portion defining a female linking structure, the second fastening portion coupling the second coupling element with the boot at the boot connection point, the first and second linking portions being cooperatively engageable, the boot and knee brace being attachable and detachable via the first and second coupling elements, the flexible tether member being disposable in tension to mitigate rotation of the boot connection point relative to the brace connection point beyond the maximum foot range of rotation.

* * * * *